United States Patent [19]
Bird et al.

[11] Patent Number: 5,637,718
[45] Date of Patent: Jun. 10, 1997

[54] UV-ABSORBING COMPOUNDS

[75] Inventors: Graham Bird, Ascot Vale; Peter J. Chalmers, Sunbury; Neil Fitzmaurice, Malvern; David J. Rigg, East Hawthorn; San H. Thang, Oakleigh South, all of Australia

[73] Assignees: ICI Australia Operations Proprietary Ltd., Melbourne; Australian Institute of Marine Science, Cape Ferguson, both of Australia

[21] Appl. No.: 109,989

[22] Filed: Aug. 23, 1993

Related U.S. Application Data

[63] Continuation of Ser. No. 752,670, Oct. 30, 1991, abandoned.

[30] Foreign Application Priority Data

Feb. 23, 1989 [AU] Australia .................................. PJ 2891
Feb. 23, 1989 [AU] Australia .................................. PJ 2892

[51] Int. Cl.$^6$ .................................................. C07D 211/74
[52] U.S. Cl. .................................................. 546/315; 546/16
[58] Field of Search ................................ 546/316, 315.16; 514/350

[56] References Cited

FOREIGN PATENT DOCUMENTS 0002251  4/1988  WIPO .................................. 546/316

OTHER PUBLICATIONS

Chemical Abstracts, vol. 114, No. 11, Abstract No. 101, 744y, Mar. 18, 1991, p. 723.

*Primary Examiner*—Zinna Northington Davis
*Attorney, Agent, or Firm*—Cushman Darby & Cushman, Intellectual Property Group of Pillsbury Madison & Sutro, LLP

[57] ABSTRACT

The invention provides UV-absorbing compounds of formula (I)

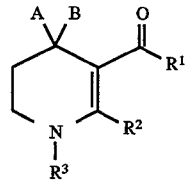

and compositions, including sunscreens, containing compounds of formula (I).

9 Claims, No Drawings

UV-ABSORBING COMPOUNDS

This is a continuation of application Ser. No. 07/752,670, filed on Oct. 30, 1991 now abandoned.

The invention relates to Ultraviolet light absorbing compounds processes for preparation thereof and compositions comprising same.

Ultraviolet light absorbing compounds are useful in protecting a range of materials from deleterious effects caused by exposure to the sun. They are used, for example, to protect skin from erythema edema and blistering and to stabilise compositions such as plastics and paint compositions.

Our copending PCT Application No PCT/AU87/00330 describes a class of UV-absorbing compounds which have a cyclic enaminoketone structure.

While such compounds have proved to be useful as UV-absorbing agents there is a need for compounds of this type which combine the features of high absorption in the appropriate region of the spectrum and have a long storage life.

Accordingly we provide a compound of formula I

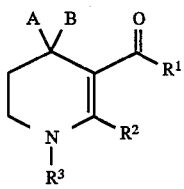

wherein $R^1$ is selected from the group consisting of $C_1$ to $C_{18}$ alkyl; $C_1$ to $C_6$ haloalkyl, $C_1$ to $C_{12}$ alkyl substituted with a substituent selected from hydroxy, amino, $C_1$ to $C_{16}$ alkoxy, $C_1$ to $C_{16}$ alkanoyl, ($C_1$ to $C_{16}$ alkoxy)-carbonyl, phenyl and the radical of formula I(a)

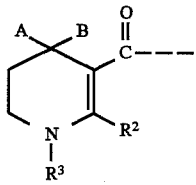

wherein A, B, $R^2$ and $R^3$ are as herein defined; $C_2$ to $C_{18}$ alkenyl; $C_5$ to $C_7$ Cycloalkyl; phenyl; the groups phenyl and benzyl said groups being substituted in the benzene ring with a substituent selected from $C_1$ to $C_9$ alkyl, $C_2$ to $C_9$ alkenyl and $C_1$ to $C_9$ alkoxy; and wherein $R^1$ and $R^2$ may form a carbocyclic ring by the bridging group of formula —$CH_2(R^7R^8C)CH_2$— wherein $R^7$ and $R^8$ are independently selected from hydrogen and $C^1$ to $C^6$ alkyl;

$R^3$ is selected from the group consisting of $C_1$ to $C_{18}$ alkyl; $C_1$ to $C_{12}$ alkyl substituted with a substituent selected from the group consisting of hydroxy, amino, $C_1$ to $C_{16}$ alkoxy, phenyl and $C_1$ to $C_{16}$ alkanoyl; $C_2$ to $C_{18}$ alkenyl; $C_5$ to $C_7$ cycloalkyl; substituted benzyl wherein the benzene ring is substituted with a substituent selected from $C_1$ to $C_9$ alkyl, $C_2$ to $C_9$ alkenyl and $C_1$ and $C_9$ alkoxy;

$R^2$ is selected from the group consisting of hydrogen and $C_1$ to $C_4$ alkyl A and B are independently selected from $C_1$ to $C_6$ alkyl and $C_1$ to $C_6$ haloakyl and may together form a carbocyclic ring of from 3 to 6 ring members.

Preferred $R^1$ include $C_1$ to $C_{18}$ alkyl; $C_1$ to $C_6$ haloalkyl; $C_1$ to $C_6$ alkyl substituted by a substituent selected from the group consisting of $C_1$ to $C_9$ alkoxy, $C_1$ to $C_9$ alkanoyl, ($C_1$ to $C_9$ alkoxy)-carbonyl and the radical of formula I(a).

More preferably $R^1$ is $C_1$ to $C_{18}$ alkyl or $C_1$ to $C_4$ haloakyl. Specific examples of $R^1$ include methyl, ethyl, n-propyl, 1-methylethyl, 1-ethylpropyl, 2-ethylpropyl, butyl, 1-methylbutyl, 2-methylbutyl, 3-methylbutyl, 3,3-dimethylbutyl, 1,1-dimethylbutyl, 2,3-dimethylbutyl, pentyl, 1-methylpentyl, trifluoromethyl and pentafluoroethyl, hexyl, heptyl, nonyl, decanyl, tridecanyl, tetradecanyl, pentadecanyl.

Preferred $R^2$ is hydrogen.

Preferred $R^3$ include $C_1$ to $C_{18}$ alkyl and more preferably $C_2$ to $C_{18}$ alkyl. Specific examples of $R^3$ include ethyl, propyl, 1-methylethyl, 1-methylpropyl, 2-methylpropyl, butyl, 1-methylbutyl, 2-methylbutyl, 3-methylbutyl, 1,1-dimethylbutyl, 3,3-dimethylbutyl, pentyl, 2-methylpentyl, hexyl, heptyl, 2-ethylhexyl, octyl, decyl and tetradecyl.

Preferably A and B are independently selected from $C_1$ to $C_4$ alkyl and most preferably A and B are methyl.

Although compounds of formula I may be used in a range of applications such as plastic and paint formulations they are particularly suited to use as UV absorbing agents in sunscreen formulations for topical application to human skin. Commercial sunscreen agents are generally preferred to have a high water resistance so that a practically useful period of protection against solar radiation is provided despite immersion in water and the presence of perspiration.

We have found that compounds of the invention comprising from 14 to 31 carbon atoms provide a level of water resistance comparable with, and in many cases superior to the leading commercially available sunscreen agents. Compounds of formula I comprising from 16 to 22 carbon atoms are particularly preferred. We have found that such compound have the optimum balance of high water resistance and efficient ultra violet radiation absorption.

Water resistance of compounds of formula I may be evaluated by reference to the partition coefficient of the compounds using a non-polar solvent such as octanol in conjunction with water. The term log P, where P is the partition coefficient, where used herein refers to the log P value determined by the HPLC method of David E Leahy, Peter J Taylor and Alan R Wait, *Ouant. Struct.-Act Relat.*, 8, 17–31 (1989) at pages 23 and 24. Log P may be used to directly compare the lipophilicity of a variety of molecules as described by Hansch, C., and Leo, A. J., *Substituent Constants for Correlation Analysis in Chemistry and Biology*, John Wiley, New York 1979.

It is preferred that in the compounds of formula I the group $R^3$ is $C_2$ to $C_{18}$ alkyl. Compounds of formula I wherein $R^3$ is $C_2$ to $C_{18}$ alkyl have generally been found to be more stable than their methyl substituted counterparts and generally more convenient to prepare via the intermediate of formula VII.

We thus further provide a compound of formula VII wherein $R^2$ is as herein before defined and $R^3$ is $C_2$ to $C_{18}$ alkyl.

Preferably compounds of the invention have a log P in the range of from 3.2 to 10.9. We have found that compounds in this range generally have a good balance of absorbance and water resistance properties.

In order to provide the correct balance of absorbance and water resistance it is particularly preferred that one of the groups $R^1$ and $R^3$ be selected from $C_1$ to $C_6$ alkyl (preferably $C_1$ to $C_4$ alkyl) and the other is $C_5$ to $C_{18}$ alkyl.

Specific examples of compound of the invention are listed in Table 1 below.

TABLE 1

| Compound No. | A, B | R¹ | R² | R³ |
|---|---|---|---|---|
| 1 | Me Me | Et | H | i-Bu |
| 2 | Me Me | Me | H | i-Bu |
| 3 | Me Me | Pr | H | i-Bu |
| 4 | Me Me | CF₃ | H | i-Bu |
| 5 | Me Me | heptyl | H | i-Bu |
| 6 | Me Me | Et | H | palmityl |
| 7 | Me Me | heptyl | H | Et |
| 8 | Me Me | Et | H | o-ethylhexyl |
| 9 | Me Me | Nonyl | H | Et |
| 10 | Me Me | pentadecanyl | H | Et |
| 11 | Me Me | tridecanyl | H | Me |
| 12 | Me Me | heptyl | H | heptyl |
| 13 | Me Me | 2-ethylhexyl-propan-3-yloate | H | Et |
| 14 | Me Me | nonyl | H | Pr |
| 15 | Me Me | nonyl | H | i-Pr |
| 16 | Me Me | nonyl | H | i-Bu |
| 17 | Me Me | undecanyl | H | Me |
| 18 | Me Me | Et | H | Decanyl |
| 19 | Me Me | heptyl | H | cyclohexyl |
| 20 | Me Me | nonyl | H | t-Bu |
| 21 | Me Me | heptyl | H | t-Bu |
| 22 | Me Me | pentyl | H | t-Bu |
| 23 | Me Me | heptyl | H | i-Pr |
| 24 | Me Me | * | H | i-Bu |
| 25 | Me Me | pentyl | H | i-Pr |
| 26 | Me Me | pentyl | H | i-Bu |
| 27 | Me Me | Et | H | t-Bu |
| 28 | Et Et | nonyl | H | i-Pr |
| 29 | Me Me | 2-decanyloxyethyl | H | i-Bu |
| 30 | Me Me | nonyl | Me | i-Pr |
| 31 | Me Me | hexyl | H | benzyl |
| 32 | Me Me | 2-hexenyl | H | i-Pr |

*is the radical of formula -

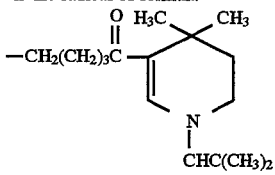

In the above table the following common abbreviations are used:

| | |
|---|---|
| Me is methyl | i-Pr is iso-propyl |
| Et is ethyl | i-Bu is iso-butyl |
| Pr is propyl | t-Bu is tert-butyl |
| Bu is butyl | |

The compounds of the invention may be prepared by a variety of methods.

It is preferred that the compounds of the invention are prepared by reaction of a compound of formula VII with an acylating agent of formula VIII or IX.

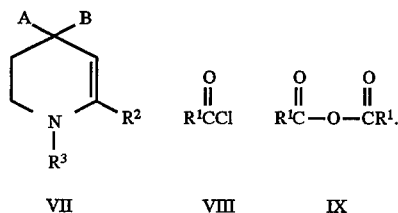

Compounds of formula VII wherein $R^3$ is $C_2$ to $C_{18}$ alkyl have good stability and are particularly suited to preparation of compounds of formula I. We further provide a compound of formula VII wherein $R^3$ is $C_2$ to $C_{18}$ alkyl and $R^1$, $R^2$, A and B are as hereinbefore defined.

We have found that the intermediate compounds of formula VII may be conveniently prepared in good yield by reaction of the appropriate substituted amino compound with a suitable α-pyrone or substituted pentanoic acid derivative.

Thus we further provide a process for preparation of a compound of formula I comprising reacting an amine of formula II with a compound of formula III,

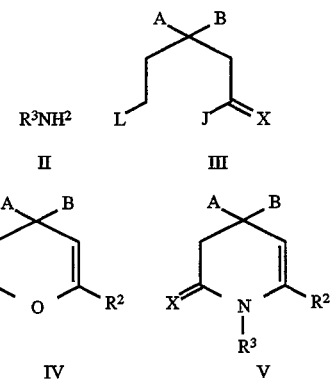

or reacting the amine of formula 11 with the α-pyrone of formula IV to provide an α-pyridone of formula V and reducing the α-pyridone; to provide the compound of formula VII. In the compounds of formulae III, IV and V the group X is oxo or a derivative thereof such as an acetal derative.

In the compound of formula III the group L is leaving group and J is selected from the group consisting of hydrogen, hydroxy, chloro and alkoxy. Preferably J is hydrogen, hydroxy or $C_1$ to $C_6$ alkoxy and most preferably J is hydrogen.

Examples of leaving groups may include alkylsulfonyl, chlorine, bromine or iodine, mesylate, tosylate, arenesulphonylates and the group where L forms an oxirane, that is, where the compound of formula III has the formula III(a)

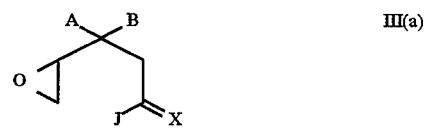

Preferably L is bromine or L forms an oxirane to provide the compound of formula III(a).

Preferred X are oxo, di-($C_1$ to $C_4$ alkoxy), ethylenedioxy, propylenedioxy and 2,2-dimethylpropylenedioxy.

When X is oxo J is typically hydrogen, hydroxy or alkoxy and when X is a derivative of oxo such as an acetal derivative then J is typically hydrogen.

Specific examples of compounds of formula III include the following:

| L | A, B | X | J |
|---|---|---|---|
| Br | Me Me | O | H |
| Br | Me Me | di-OEt | H |
| Br | Me Me | —O—CH₂CH₂—O— | H |
| OTs | Me Me | O | H |
| Br | Me Me | O | OCH₃ |
| Br | Me Me | O | Cl |
| Br | Me Me | —OCH₂C(CH₃)₂CH₂O— | H |
| Br | Me Me | —O(CH₂)₃O— | H |

Note:
OTs is tosylate

Compounds of formula III are believed to be novel compounds, hence, in a further embodiment of the invention we provide compounds of formula III.

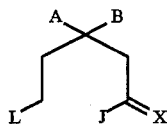

III wherein L, A, B, J and X are as hereinbefore defined.

The compound of formula III may be prepared by substitution of an olefin of formula XIII.

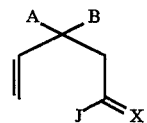

XIII

For example, compounds of formula III where L is Bromine may be prepared by reaction of compounds of formula X with gaseous hydrogen bromide in the presence of a free radical initiator (anti-Markovniknov).

The compounds of the invention may also be prepared by a method involving the following steps:

(a) Reacting a glutaric anhydride derivative of formula X with an amine of formula II to form an imice of formula XII.

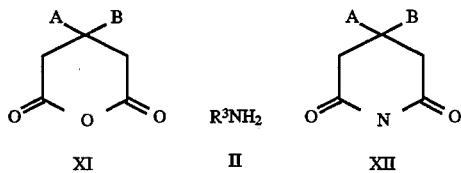

XI  II  XII (b) reducing the imide of formula XII using a suitable reducing agent such as lithium aluminium hydride to give a cyclic amine of formula VI.

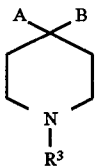

VI (c) Oxidising the amine of formula VI to form the enamine of formula VII wherein $R^2$ is H. The preferred oxidizing agent for this reaction is mercuric acetate.

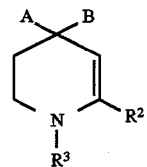

VII (d) Acylating the compound of formula VII using an acyl chloride of formula VIII or anhydride of formula IX to provide the compound of the invention of formula I.

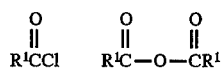

VIII  IX

One or more compounds of the invention may be used to reduce the exposure of a surface such as skin to ultraviolet radiation by topical application thereto.

The invention further provides an ultraviolet light absorbing composition comprising as an effective component thereof at least one compound of formula 1.

The level of the UV-absorbing agent of the invention in the compositions is preferably in the range of from 0.001 to 30% w/w of the total composition although the preferred concentration will of course depend on the nature of the composition and the degree of screening required.

In one embodiment of the invention the UV-absorbing composition is a sunscreen composition for topical application to a surface such as skin. Such compositions may be in a variety of forms such as for example solids, liquids, gels or aerosols and will generally comprise a carrier which adapts the agent for topical application.

Examples of suitable carriers may include oils, for example mineral oils, paraffin, squaline and octyl palmitate and oil/alcohol mixtures.

In one embodiment the sunscreen composition is an emulsion such as a oil-in-water emulsion which may for example comprise a water-insoluble liquid (eg paraffin oil) as the oil phase.

Further components such as perfumes, colouring agents, antioxidants and oxygen scavengers may be used in the composition of the invention. The composition may comprise additives making the composition useful as a cosmetic or topical pharmaceutical.

Typically the compounds of the invention will constitute in the range of 0.5 to 30% (preferably 1.0 to 15%) by weight of the total sunscreen composition. However higher or lower concentrations may be used if desired depending on the degree of screening required.

In a further embodiment there is provided a method of preparing a sunscreen composition comprising mixing at least one compound of formula I with a carrier suitably adapted to allow application of said compound to a surface. The temperature at which the composition is prepared may vary depending on the components but is generally in the range of from 5 to 100° C.

In another embodiment of the invention the UV-absorbing composition is a coating composition such as a paint composition, preferably comprising in the range of from 0.001 to 5% w/w of at least one compound of formula I. Typically a paint composition will comprise a binder or film forming component such as alkyd resin, acrylic latex or urethane and may comprise a pigment to provide colouration and/or other optional additives such as fungicides, flow control agents and rheology modifiers.

In another embodiment we provide a plastics composition comprising at least one UV-absorbing agent of formula I.

The base plastic may be any plastic in which protection against UV-induced degradation is desired. The plastic composition will generally comprise a polymeric component and in the range of 0.01 to 45% w/w of the UV-absorbing agent component and may comprise other components, such as one or more of fillers, antioxidants and lubricants, which are known in the art.

The invention will now be described but is in no way limited to the following Examples.

EXAMPLE 1

(a) Preparation of 5 Bromo-3,3-dimethylpentanal 1,1-Diethoxy-3,3-dimethylpent-4-ene was prepared from 3,3-dimethylpent-4-enal, ethanol and hydrogen chloride gas by the method used for the preparation of its dimethoxy analogue derivative described in the literature (Boeckman and Ko, *J. Am. Chem. Soc.*, 104, 1982, p. 1033). $^1$H NMR (CDCl$_3$) δ5.81 (1H, dd, J 10, 18H$_z$), 4.90 (1H, dd, J 2.0, 18.0H$_z$), 4.89 (1H, dd, J 2.0, 10.0H$_z$), 4.48 (1H, t, J 5.0H$_z$), 3.55 (2H, q, J 7.0H$_z$), 3.47 (2H, q, J 7.0H$_z$), 1.64 (2H, d, J 5.0H$_z$), 1.18 (6H, t, J 7.0H$_z$), and 1.04 (6H, s).

(b) Hydrogen bromide gas was bubbled through a solution of benzoyl peroxide (0.1 g) (or α, $α^1$-azobisisobutyronitrile, 0.1 g) and 1,1-diethoxy-3,3-dimethylpent-4-ene in dry pentane (50 ml) stirring under nitrogen at 0°–5° C.

The reaction was monitored by T.L.C. (1:1 dichloromethane: hexane as eluent) until all starting material was consumed (detected by T.L.C. as the 2,4 DNP derivatives of the corresponding aldehydes). Water (20 ml) was added, the mixture stirred vigorously for 5 minutes and the organic layer was separated and the aqueous layer extracted with further pentane (20 ml). The combined organic layer was washed with water (20 ml), dried over magnesium sulphate and concentrated to give 5-bromo-3,3-dimethyl pentanal (19.0 g) as a pale yellow oil. Distillation under reduced pressure gave colourless oil (17.0 g, 88%) (b. pt 48°–50° C. at 0.4 mbar. $^1$H NMR (CDCl$_3$) δ9.77 (1H, t, J2.0H$_z$), 3.39 (2H, m), 2.32 (2H, d, J2.0H$_z$), 1.97 (2H, m), 1.11 (6H, s).

(c) 1-(2-Methylpropyl)-4,4-dimethyl-1,4,5,6-tetrahydropyridine

Acetic acid was added to a mixture of ethanol (40 ml) and water (20 ml) until the pH was 4. 5-Bromo-3,3-dimethylpentanal (19.3 g, 0.1 mol) was added to the mixture, which was then cooled to 0°–5° C. and purged with nitrogen. Isobutylamine (7.3 g, 0.1 mol) was added over 5 minutes to the solution stirring under an atmosphere of nitrogen. After 3 hours stirring at 0°–5° C., most of the ethanol was removed under reduced pressure, the residue then diluted with water (20 ml) and the solution taken to pH 10 with solid potassium carbonate. The mixture was extracted with ether (3×50 ml), the organic layer dried over anhydrous MgSO$_4$ and concentrated to yield a pale yellow oil (15.5 g, 93%) which was essentially pure by $^1$H NMR spectroscopy. A pure colourless liquid (13.0 g, 78%) was obtained after vacuum distillation, b.p. 50°–53° C./2 mm Hg. The $^1$H NMR spectrum was found to be the same as for material prepared by the procedure hereafter described in Example 25 Part (C).

(d) I-(2-Methylpropyl)-3-propionyl-4,4-dimethyl-1,4,5,6-tetrahydropyridine

Propionyl chloride (9.25 g, 0.1 mol) was added dropwise to a solution of 1-(2-methylpropyl)-4,4-dimethyl-1,4,5,6-tetrahydropyridine (16.7 g, 0.1 mol) and triethylamine (12.1 g, 0.12 mol) in dichloromethane (100 ml) stirring under an atmosphere of nitrogen at ice bath temperature. After one hour at this temperature, water (50 ml) was added, the organic layer was separated, washed with 5% aqueous sodium carbonate and dried over anhydrous MgSO$_4$. Removal of the organic solvent afforded a yellow oil (22.3 g, quantitative) which was essentially pure by 90 MHz NMR spectroscopy. After column chromatography on silica-gel (Merck Kieselgel 60, 70–230 mesh) using 5% diethyl ether in dichloromethane (or 3:7 ether: n-hexane) as eluent, the pure 1-(2-methylpropyl)-3-propionyl-4,4-dimethyl-1,4,5,6-tetrahydropyridine (18.0 g, 81%) was obtained as a very pale yellow oil. UV λ max MeOH 307 nm, 29,300. $^1$H NMR (CDCl$_3$) δ7.13 (1H, s), 3.10 (2H, m, AA$^I$XX$^I$ system), 2.94 (2H, d, J7.4H$_z$), 2.44 (2H, q, J7.5H$_z$), 1.95 (1H, m, J6.6H$_z$, J7.4H$_z$), 1.60 (2H, m, AA$^I$XX$^I$ system), 1.27 (6H, s), 1.08 (3H, t, J7.5 J$_z$), and 0.90 (6H, d, J6.6H$_z$). $^{13}$C NMR (CDCl$_3$) δ195.9 (s), 147.9 (d), 114.4 (s), 64.1 (t), 43.3 (t), 39.3 (t), 30.0 (s), 29.7 (t), 28.1 (q), 27.4 (d), 19.8 (q), and 10.3 (q). MS 223.1913 (M$^+$), 25.2%, 194 (100%).

EXAMPLES A to J

The compounds of these examples were prepared by the method of Example 1 with the appropriate amine shown in the table 2 below being substituted for isobutylamine in Example 1 part (e).

| Example | Amine | Product Name |
|---|---|---|
| A | palmitylamine | 1-palmityl-4,4-dimethyl-1,4,-5,6-tetrahydropyridine |
| B | ethylamine | 1-ethyl-4,4-dimethyl-1,4,5,6-tetrahydropyridine |
| C | 2-ethylhexylamine | 1-(2-ethylhexyl)-4,4-dimethyl-1,4,5,6-tetrahydropyridine |
| D | methylamine | 1,4,4-trimethyl-1,4,5,6-tetrahydropyridine |
| E | heptylamine | 1-heptyl-4,4-dimethyl-1,4,5,6-tetrahydropyridine |
| F | isopropylamine | 1-(1-methylethyl)-4,4-dimethyl-1,4,5,6-tetrahydropyridine |
| G | propylamine | 1-propyl-4,4-dimethyl-1,4,5,6-tetrahydropyridine |
| H | decylamine | 1-decyl-4,4-dimethyl-1,4,5,6-tetrahydropyridine |
| I | cyclohexylamine | 1-cyclohexyl-4,4-dimethyl-1,4,5,6-tetrahydropyridine |
| J | tert-butylamine | 1-(1,1-dimethylethyl)-4,4-dimethyl-1,4,5,6-tetrahydropyridine |

EXAMPLES 2 to 23

The compounds of examples 2 to 23 were prepared by reaction of the corresponding tetrahydropyridine intermediate identified in table 4 with the appropriate acid chloride identified in the table 4 using the procedure of Example 1 to provide the product as detailed in Table 4.

TABLE 4

| Example | Intermediate Example No. | Acid Chloride | Product Compound No. | Name |
|---|---|---|---|---|
| 2 | 1(c) | acetyl | 2 | 1-(2-Methylpropyl)-3-acetyl-4,4-dimethyl-1,4,5,6-tetrahydropyridine |

TABLE 4-continued

| Example | Intermediate Example No. | Acid Chloride | Product Compound No. | Name |
|---|---|---|---|---|
| 3 | 1(c) | butyryl | 3 | 1-(2-Methylpropyl)-3-butyryl-4,4-dimethyl-1,4,5,6-tetrahydropyridine |
| 4 | 1(c) | trifluoro-acetyl | 4 | 1-(2-Methylpropyl)-3-trifluoroacetyl-4,4-dimethyl-1,4,5,6-tetrahydropyridine |
| 5 | 1(c) | octanoyl | 5 | 1-(2-Methylpropyl)-3-octanoyl-4,4-dimethyl-1,4,5,6-tetrahydropyridine |
| 6 | A | propionyl | 6 | 1-Palmityl-3-propionyl-4,4-dimethyl-1,4,5,6-tetrahydropyridine |
| 7 | B | octanoyl | 7 | 1-Ethyl-3-octanoyl-4,4-dimethyl-1,4,5,6-tetrahydropyridine |
| 8 | C | propionyl | 8 | 1-(2-Ethylhexyl)-3-propionyl-4,4-dimethyl-1,4,5,6-tetrahydropyridine |
| 9 | B | decanoyl | 9 | 1-Ethyl-3-decanoyl-4,4-dimethyl-1,4,5,6-tetrahydropyridine |
| 10 | B | palmitoyl | 10 | 1-Ethyl-3-palmitoyl-4,4-dimethyl-1,4,5,6-tetrahydropyridine |
| 11 | D | myristoyl | 11 | 1-Methyl-3-myristoyl-4,4-dimethyl-1,4,5,6-tetrahydropyridine |
| 12 | E | octanoyl | 12 | 1-Heptyl-3-ocatanoyl-3,4-dimethyl-1,4,5,6-tetrahydropyridine |
| 13 | B | 2-ethylhexyl succinoyl | 13 | 1-Ethyl-3(2-ethyl-hexylsuccinoyl)-4,4-dimethyl 1,4,5,6-tetrahydropyridine |
| 14 | G | decanoyl | 14 | 1-Propyl-3-decanoyl-4,4-dimethyl-1,4,5,6-tetrahydropyridine |
| 15 | F | decanoyl | 15 | 1-(-Methylethyl)-3 decanoyl-4,4-dimethyl 1,4,5,6-tetrahydropyridine |
| 16 | 1(c) | decanoyl | 16 | 1-(2-Methylpropyl)-3-decanoyl-4,4-dimethyl-1,4,5,6-tetrahydropyridine |
| 17 | D | lauroyl | 17 | 1-Methyl-3-lauroyl-4,4-dimethyl 4,5,6-tetrahydropyridine |
| 18 | H | propionyl | 18 | 1-Decyl-3-propionylo-4,4-dimethyl-1,4,5,6-tetrahydropyridine |
| 19 | I | octanoyl | 19 | 1-Cyclohexyl-3-octanoyl-4,4-dimethyl 1,4,5,6- |

TABLE 4-continued

| Example | Intermediate Example No. | Acid Chloride | Product Compound No. | Name |
|---|---|---|---|---|
| 20 | J | decanoyl | 20 | 1-(1,1-Dimethyl-ethyl)-3-decanoyl-4,4,-dimethyl-1,4,5,6-tetrahydropyridine |
| 21 | J | octanoyl | 21 | 1-(1,1-Dimethyl-ethyl)-3-octanoyl-4,4-dimethyl-1,4,5,6-tetrahydropyridine |
| 22 | J | hexanoyl | 22 | 1-(1,1-Dimethyl-ethyl)-3-hexanoyl-4,4-dimethyl-1,4,5,6-tetrahydropyridine |
| 23 | F | octanoyl | 23 | 1-(1-Methylethyl)-3-octanoyl-4,4-dimethyl-1,4,5,6-tetrahydropyridine |

The proton nuclear magnetic resonance spectra and ultra violet spectra of compounds 1 to 23 were measured and are recorded in Table 5 (except where indicated by a hyphen).

EXAMPLE 24

1,1'-(2-Methylpropyl)-3,3'-adipoyl-1.1'-dimethyl-bis(1,4,5,6-tetrahydropyridine) (24)

The title compound was prepared in accordance with the procedure of Example 1 Part (C) replacing propionyl chloride with adipoyl chloride with the exception that, due to the stoichiometry of the reaction, an approximate molar ratio of adipoyl chloride: 1-(2-Methylpropyl)-4,4-dimethyl-1,4,5,6-tetrahydropyridine of 1:2 was used. The proton nuclear magnetic responance spectrum and ultra violet spectrum of the product was measured and is recorded in Table 5.

TABLE 5

| Compound | Appearance | UV (Methanol) λ Max (n.m.) | ε | Proton Chemical Shift in ppm [CDCl$_3$] |
|---|---|---|---|---|
| 1 | oil | 307 | 29,300 | 7.13(s, 1H); 3.10(m, 2H); 2.94(d, 2H); 2.44(q, 2H); 1.95(m, 1H); 1.60(m, 2H); 1.27(s, 6H); 1.08(t, 3H); 0.90(d, 6H). |
| 2 | oil | 307 | 30,790 | 7.10(s, 1H); 3.10(m, 2H); 2.95(d, 2H); 2.10(s, 3H); 2.00(m, 1H); 1.60(m, 2H); 1.27(s, 6H); 0.90(d, 6H). |
| 3 | oil | — | — | 7.10(s, 1H); 3.10(m, 2H); 2.95(d, 2H); 2.45(t, 2H); 1.95(m, 1H); 1.60(m, 4H); 1.27(s, 6H); 1.05(t, 3H); 0.90(d, 6H). |
| 4 | oil | 315 | — | 7.35(s, 1H); 3.20(t, 2H); 3.05(d, 2H); 1.95(m, 1H); 1.56(t, 2H) 1.30(s, 6H); 0.90(d, 6H). |
| 5 | oil | 307 | 30,600 | 7.12(s, 1H); 3.10(t, 2H); 2.95(d, 2H); 2.39(t, 2H); 1.95(m, 1H); 1.62–0.85 (m, 27H) |
| 6 | oil | 306 | 27,090 | 7.15(s, 1H); 3.10(m, 4H); 2.42(q, 2H); 1.55(m, 4H); 1.25(bs, 32H); 1.15–0.80 (m, 6H). |
| 7 | oil | 307 | 24,330 | 7.16, (S, 1H); 3.22 (q, 2H); 3.10(t, 2H); 2.40(t, 2H); 1.62–0.89(m, 23H). |
| 8 | oil | 307 | 26,038 | 7.14(s, 1H); 3.09(m, 2H); 3.04(d, 2H); 2.44(q, 2H); 1.59(m, 4H); 1.27(bs, 12H); 1.10(q, 4H); 0.89(t, 6H). |
| 9 | oil | 307 | 28,730 | 7.16(s, 1H); 3.22(q, 2H); 3.10(m, 2H); 2.40(t, 2H); 1.58(m, 4H); 1.26(bs, 18H); 1.20(t, 3H); 0.87 (t, 3H). |
| 10 | oil | 307 | 24,200 | 7.15(s, 1H); 3.22(q, 2H); 3.11(t, 2H); 2.39(t, 2H); 1.62–0.85(m, 40H). |
| 11 | oil | — | — | 7.09(s, 1H); 3.05(t, 2H); 2.98(s, 3H); 2.39(t, 2H); 1.62–0.85(m, 33H). |
| 12 | oil | — | — | 7.14(s, 1H); 3.12(m, 4H); 1.61–0.85(m, 34H). |
| 13 | oil | 307 | 26,680 | 7.25(s, 1H); 3.98(d, 2H); 3.23(q, 2H); 3.12(t, 2H); 2.78(t, 2H); 2.62(t, 2H); 1.63–0.85(m, 28H). |
| 14 | oil | 307 | 27,900 | 7.15(s, 1H); 3.12(m, 4H); 2.39(t, 2H); 1.62(m, 6H); 1.26(bs, 18H); 0.89(m, 6H). |
| 15 | oil | 306 | 27,550 | 7.24(s, 1H); 3.46(m, 1H); 3.07, (t, 2H); 2.40(t, 2H); 1.59–0.84(m, 31H). |
| 16 | oil | 306 | 22,600 | 7.11(s, 1H); 3.09(t, 2H); 2.94(d, 2H); 2.36(t, 2H); 1.95(m, 1H); |

TABLE 5-continued

| Compound | Appearance | λ Max (n.m.) | ε UV (Methanol) | Proton Chemical Shift in ppm [CDCl₃] |
| --- | --- | --- | --- | --- |
| 17 | oil | 308 | 22,820 | 1.64–0.85(m, 31H). 7.10(s, 1H); 3.07(t, 2H); 2.94(d, 2H); 2.36(t, 2H); 1.95(m, 1H); 1.64–0.85(m, 31H). |
| 18 | oil | 307 | 28,200 | 7.15(s, 1H); 3.11(m, 4H); 2.43(q, 2H); 1.63–0.85(m, 30H). |
| 19 | oil | — | — | 7.24(s, 1H); 3.77(m, 1H); 3.11(t, 2H); 2.40(t, 2H); 1.64–0.86(m, 31H). |
| 20 | solid mpt 60–62° C. | 306 | 29,480 | 7.52(s, 1H); 3.15(t, 2H); 2.40(t, 2H); 1.62–0.89(m, 34H). |
| 21 | solid mpt 63–64° C. | 306 | 30,280 | 7.51(s, 1H); 3.16(t, 2H); 2.42(t, 2H); 1.65–0.89(m, 30H). |
| 22 | oil | — | — | 7.52(s, 1H); 3.15(m, 2H); 2.40(t, 2H); 1.66–0.89(m, 26H). |
| 23 | oil | 305 | 28,000 | 7.28(s, 1H); 3.47(m, 1H); 3.08(t, 2H); 2.40(t, 2H); 1.57(t, 4H); 1.28–0.89 (m, 23H). |
| 24 | oil | 310 | 44,300 | 7.22(s, 2H); 3.60(t, 2H); 3.14(m, 4H); 3.01(d,4H); 2.52(m, 2H); 2.30—1.78 (m, 6H); 1.62(t, 4H) 1.25 (d, 2H); 0.95(d, 6H); 0.91 (d, 6H). |

EXAMPLE 25

This example demonstrates an alternative procedure for preparation of compounds of the invention of formula I.

The Compound 1-(2-methylpropyl)-4,4-dimethyl-1,4,5,6-tetrahydropyridine was prepared by the following procedure.

(a) N-(2-Methylpropyl)-3,3-dimethylglutarimide

Isobutylamine (7.3 g, 0.1 mol) was added slowly to 3,3-dimethylglutaric anhydride (14.2 g, 0.1 mol) stirring at room temperature in a two neck round bottom flask fitted with a water condenser. After 30 minutes, acetic anhydride (20.4 g, 0.2 mol) was added, and the resulting mixture was boiled for two hours. After cooling, the mixture was poured slowly on to an aqueous NaOH solution (2N, 100 ml) stirring at room temperature. After one hour, the mixture was diluted with diethyl ether (50 ml), and the organic layer was separated. The aqueous layer was washed with more diethyl ether (2×50 ml), and the combined organic layer dried and concentrated to give the title compound as a pale yellow oil which solidified on standing, m.p. 48°–52° C., yield 18.5 g (94%). The product was sufficiently pure by NMR spectroscopy to be used directly in the following procedure.

(b) 1-(2-Methylpropyl)-4,4-dimethylpiperidine

A solution of N-(2-Methylpropyl)-3,3-dimethylglutarimide (19.5 g, 0.0984 mol) in dry ether (30 ml) was added via a dropping funnel over 30 minutes to a suspension of lithium aluminum hydride (5.36 g, 0.141 mol) in dry ether (50 ml) at 0° C. stirring under nitrogen. The mixture was then boiled for 3 hours, allowed to cool to room temperature and the excess lithium aluminium hydride was decomposed by careful addition of solid sodium sulphate decahydrate (20 g). After the suspended solid had turned white, the mixture was filtered, the solid washed twice with ether (2×50 ml), and the combined filtrate concentrated to yield a colourless liquid. Distillation gave the pure product, (1-(2-methylpropyl)-4,4-dimethylpipeidine, 13.0 g (82%), b.p. 81°–82° C./16 mmHg. ¹H NMR (CDCl3) δ2.30 (4H, t), 2.05 (2H, d), 1.80 (1H, m), 1.35 (4H, t), 0.90 (6H, s) and 0.85 (6H, d).

(c) 1-(2-Methylpropyl)-4,4-dimethyl-1,4,5,6-tetrahydropyridine

A solution of 1-(2-Methylpropyl)-4,4-dimethylpiperidine (13.0 g, 0.077 mol) and mercuric acetate (98.8 g, 0.31 mol, 4 molar equivalent) in 5% aqueous acetic acid (300 ml) was boiled for 2.5 hours. On cooling, the white solid (mercurous acetate) was filtered-off, and the filtrate was treated repeatedly with hydrogen sulphide gas (3×), each time the mixture was filtered through a celite pad, the final filtrate made basic to pH 10 with K₂CO₃. The aqueous layer was extracted with ether (3×100 ml), and the combined organic layers dried over anhydrous MgSO₄, concentrated and distilled to give the product, 1-(2-methylpropyl)-4,4-dimethyl-1,4,5,6-tetrahydropyridine, 7.1 g (55%), b.p. 50°–53° C. (2 mmHg). 1HNMR (CDCl₃) δ5.73 (IH, d), 4.05 (1H, d), 2.88 (2H, t), 2.55 (2H, d), 1.80 (1H, m), 1.55 (2H, t), 0.95 (6H, s), and 0.85 (6H, d).

EXAMPLE 26

This example demonstrates an alternative procedure for preparation of formula III which may be used in preparation of compounds of formula I.

The compound 5-bromo-3,3-dimethyl pentanal was prepared by the following procedure which may be used in place of the procedure of Example 1 Part (a) in preparing compounds of the invention such as for example compounds 1 to 32 inclusive.

(a) 3,3-Dimethylpent-4-enoic Acid

To a solution of methyl 3,3-dimethylpent-4-enoate (0.5 mole) in 500 ml of ethanol (95% grade) was added potassium hydroxide (1 mole). The solution was refluxed for 1.5 hours. After cooling down to room temperature, the solution was concentrated to 200 ml on a rotary evaporator, and acidified by the addition of 5N H2SO4 solution. The product was isolated by extraction with diethyl ether (3×200 mls). After removal of the solvent, the crude product was distilled under reduced pressure to yield the pure acid (77%) b.p. 78°–80° C. (1.5 mmHg). ¹H NMR (CDCl₃) δ10.60 (1H, broad s), 5.90 (1H, dd, J 10.3, 17.6 Hz), 5.00 (1H, dd, J 17.6 Hz, J 1.3 Hz), 4.97 (1H, dd, J 10.3 Hz, J 1.3 Hz), 2.35 (2H, s), and 1.20 (6H, s).

(b) 5-Bromo-3,3-dimethylpentanoic Acid

A stream of dry hydrogen bromide gas (made from 83.3 m) of tetralin and 71 ml of bromine) was bubbled through a stirred solution of 3,3-dimethylpent-4-enoic acid (80 g, 0.625 mol) in dry light petroleum b.p. 40°–60° C. (940 ml) together with benzoyl peroxide (6.4 g, 0.025 mol) until it was saturated (about 2 hours) whilst the reaction mixture was maintained at the temperature between 10°–20° C. by occasional cooling. After completion of the reaction, the mixture was cooled down to −10° C. and the solid product was collected (near quantitative yield). The product was sufficiently pure by NMR spectroscopy to be used directly in the next step synthesis. However, a pure product was obtained after recrystallised from light petroleum spirit m.p. 53°–55° C. ¹H NMR δ3.43 (2H, t), 2.27 (2H, s), 2.10 (2H, t), and 1.08 (6H, s).

(c) 5-Bromo-3,3-dimethylpentanoyl chloride

5-Bromo-3,3-dimethylpentanoic acid (40 g, 0.192 mol) was converted into the corresponding acid chloride by heating it on a water bath with thionyl chloride (29.6 g, 1.3 equivalents). The title compound was obtained by vacuum distillation as a colourless liquid, 38.8 g (89% yield), b.p. 77° C./0.75 mm Hg. $^1$H NMR (CDCl$_3$) δ3.40 (2H, t), 2.85 (2H, s), 2.00 (2H, t), and 1.10 (6H, s).

(d) 5-Bromo-3,3-dimethylpentanal

The title compound was prepared by the Rosenmund reduction of 5-bromo-3,3-dimethylpentanoyl chloride using a similar procedure described in the literature (Burgstahler, Weigel and Shaefer, *Synthesis*, 1976, p. 767). The pure 5-bromo-3,3-dimethylpentanal was obtained as a colourless oil after distillation, b.p. 48 –50° C. (0.3 mm Hg). $^1$H NMR (CDCl$_3$) δ9.77 (1H,t, J 2.0 Hz), 3.39 (2H, m), 2.32 (2H, d, J 2.0 Hz), 1.97 (2H, m), and 1.11 (6H, s).

In an alternative procedure the title compound was prepared by the Rosenmund reduction of 5-bromo-3,3-dimethylpentanoyl chloride using a similar procedure as described in Vogel, Practical Organic Chemistry, p. 765.

The experiment was designed and set-up as indicated in the above reference.

5-Bromo-3,3-dimethylpentanoyl chloride (16 g, 0.070 mol) and 5% palladium-barium sulphate catalyst (0.8 g, 5% w/w) were added to dry toluene (100 ml). A slow stream of dry hydrogen gas was passed through the stirred mixture heated at reflux. The course of the reaction was followed by the rate of hydrogen chloride evolution (titration with base) until approximately 85–90% of the theoretical amount of hydrogen chloride was generated. After approximately 3 h, evolution of hydrogen chloride ceased. The reaction mixture was cooled and purged with nitrogen for 5 min. The catalyst was filtered off through a celite pad and filtrate concentrated invacu yielding 13.5 g (100%) of the title compound. The material was analysed by G.C.

EXAMPLE 27

A coating composition may be prepared by blending compound 1 prepared according to Example 1 into a standard thermosetting acrylic/melamine-formaldehyde resin system at a rate of 2% by weight. The resulting composition is useful as a clearcoat in an automotive "base coat—clearcoat" coating system.

EXAMPLE 28

A sunscreen composition for topical application to skin may be prepared by mixing the following components in the specific proportion where the sunscreen compound is compound 1.

| Sunscreen lotion composition | % w/w |
| --- | --- |
| Methyl para-hydroxy benzoate | 0.25 |
| Propyl para-hydroxy benzoate | 0.10 |
| Catyl/Stearyl 2-Ethylhexonoate | 2.00 |
| "CARBOMER" 491 thickener (cross linked acrylic acid polymer) | 0.45 |
| Phenyl trimethicone | 1.00 |
| Stearic Acid | 3.00 |
| Sodium Hydroxide | 0.15 |
| Phenoxyethanol | 0.30 |
| Isopropyl Isostearate | 5.00 |
| Antioxidant (BHA, BHT, ascorbates, tocopherols) | 0.08 |
| Glyceryl Monostearate & PEG 100 Stearate | 1.00 |
| Fragrance | 0.10 |
| Sunscreen Compound | 6.00 |
| Disodium EDTA | 0.05 |
| Treated water | 80.52 |

("CARBOMER" is a trade mark)

EXAMPLE 29

A plastics composition suitable for moulding was prepared by forming an intimate mixture of polypropylene GSM 109 (moulding grade) 0.1% w/w calcium stearate, 0.1% w/w antioxidant ("IRGANOX" B225, IRGANOX is a trade mark) and 0.1% w/w of compound 1 prepared according to Example 1.

EXAMPLE 30

A sunscreen composition for topical application to skin was prepared by mixing the following components where the sunscreen compound is compound 1.

| Water | 68.9 |
| --- | --- |
| Carbomer 941 | 0.2 |
| Isopropyl palmitate | 20.0 |
| Glyceryl stearate and PEG 100 stearate mixture | 5.0 |
| Polysorbate 60 | 5.0 |
| Sunscreen | 0.5 |
| BHT | 0.2 |
| Sodium thiosulphate | 0.2 |

The pH of the composition was adjusted to 7.

EXAMPLE 31

A sunscreen composition for topical application to skin may be prepared by mixing the following components where the sunscreen compound is compound 1.

| Sunscreen lotion composition | % w/w |
| --- | --- |
| Carbomer 934 | 0.65 |
| Ammonia (12.5% Solution) | 1.31 |
| Glyceryl stearate and PEG 100 stearate | 1.00 |
| Carnauba wax | 1.50 |
| Isostearic acid | 2.00 |
| Light liquid paraffin | 4.00 |
| Paraffin - soft white | 2.00 |
| Phenoxyethanol (and) methyl paraben (and) ethyl paraben (and) propyl paraben (and) butyl paraben | 0.80 |
| Dimethicone | 2.00 |
| Fragrance | 0.25 |
| Antioxidant (BHA, BHT, ascorbates, tocopherols) | 0.10 |
| Sunscreen compound | 10.00 |
| Microfine titanium dioxide | 5.00 |
| Water | 69.39 |

EXAMPLE 32

This example compares the ultraviolet light absorbing properties and water resistance properties of compounds of the invention.

$E_1$% is a relative measure of the UV absorbance of a 1% w/w solution of the compound.

For each compound in Table 6 below the log P was determined by the HPLC method of Leahy, Taylor and Wait *Quant, Struct, Act Relat.*, 8, 17–31 (1989) and the results are recorded in Table 6.

| Compound No. | No. Carbon Atoms | $E_1$ % | log P |
| --- | --- | --- | --- |
| 1 | 14 | 131 | 3.2 |
| 2 | 13 | 140 | 2.7 |
| 3 | 15 | 124 | 3.7 |
| 4 | 13 | 112 | 3.0 |
| 5 | 19 | 100 | 5.8 |
| 6 | 26 | 75 | 9.4 |
| 7 | 17 | 110 | 4.8 |
| 8 | 18 | 105 | 5.3 |
| 9 | 19 | 100 | 5.8 |

-continued

| Compound No. | No. Carbon Atoms | $E_1$ % | log P |
|---|---|---|---|
| 10 | 25 | 77 | 8.9 |
| 11 | 22 | 87 | 7.4 |
| 12 | 22 | 87 | 7.4 |
| 13 | 21 | 87 | 6.9 |
| 14 | 20 | 95 | 6.3 |
| 15 | 20 | 95 | 6.3 |
| 16 | 21 | 91 | 6.9 |
| 17 | 20 | 95 | 6.3 |
| 18 | 20 | 95 | 6.3 |
| 19 | 21 | 91 | 6.9 |
| 20 | 21 | 91 | 6.9 |
| 21 | 19 | 100 | 5.8 |
| 22 | 17 | 110 | 4.8 |
| 23 | 18 | 105 | 5.3 |
| 24 | 28 | 131 | 9.4 |

We claim:

1. A compound of formula I

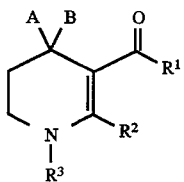

wherein

A and B are independently selected from $C_1$ to $C_6$ alkyl and $C_1$ to $C_6$ haloalkyl and wherein A and B may together form a carbocyclic ring of from 3 to 6 ring members:

$R^1$ is selected from the group consisting of $C_1$ to $C_{18}$ alkyl; $C_1$ to $C_6$ haloalkyl; $C_1$ to $C_{12}$ alkyl substituted with a substituent selected from hydroxy, amino, $C_1$ to $C_{16}$ alkoxy, $C_1$ to $C_{16}$ alkanoyl, ($C_1$ to $C_{16}$ alkoxy) carbonyl, phenyl $C_2$ to $C_{18}$ alkenyl; $C_5$ to $C_7$ cycloalkyl; phenyl; the groups substituted phenyl and substituted benzyl wherein the substituent is a benzene ring substituent and is selected from the group consisting of $C_1$ to $C_9$ alkyl, $C_2$ to $C_9$ alkenyl and $C_1$ to $C_9$ alkoxy;

$R^2$ is selected from the group consisting of hydrogen and $C_1$ to $C_4$ alkyl;

$R^3$ is selected from the group consisting of $C_1$ to $C_{18}$ alkyl; $C_1$ to $C_{12}$ alkyl substituted with a substituent selected from the group consisting of hydroxy, amino, $C_1$ to $C_{16}$ alkoxy, phenyl and $C_1$ to $C_{16}$ alkanoyl; $C_2$ to $C_{18}$ alkenyl; $C_5$ to $C_7$ cycloalkyl; and substituted benzyl wherein the benzene ring is substituted with a substituent selected from the group consisting of $C_1$ to $C_9$ alkyl, $C_2$ to $C_9$ alkenyl and $C_1$ to $C_9$ alkoxy.

2. A compound according to claim 1 wherein;

A and B are independently selected from $C_1$ to $C_6$ alkyl;

$R^1$ is selected from the group consisting of $C_1$ to $C_{18}$ alkyl, $C_1$ to $C_6$ haloalkyl and $C_1$ to $C_6$ alkyl substituted by a substitutent selected from the group consisting of $C_1$ to $C_9$ alkoxy, $C_1$ to $C_9$ alkanoyl, ($C_1$ to $C_9$ alkoxy) carbonyl;

$R^2$ is hydrogen; and $R^3$ is selected from the group consisting of $C_1$ to $C_{18}$ alkyl.

3. A compound according to claim 1 wherein:

A and B are methyl;

$R^1$ is selected from $C_1$ to $C_{18}$ alkyl;

$R^2$ is hydrogen; and $R^3$ is $C_2$ to $C_{18}$ alkyl.

4. A compound according to claim 1 wherein one of the groups $R^1$ and $R^3$ is selected from $C_1$ to $C_6$ alkyl and the other is selected from $C_4$ to $C_{18}$ alkyl.

5. A compound according to claim 4 wherein one of $R^1$ and $R^3$ is selected from $C_1$ to $C_4$ alkyl and the other is selected from $C_6$ to $C_{18}$ alkyl.

6. A compound according to claim 3 which comprises a total of from 14 to 31 carbon atoms.

7. A compound according to claim 2 wherein log P of said compound is in the range of from 3.2 to 10.9.

8. A sunscreen composition comprising an effective amount of a compound of formula I defined according to claim 1 and a carrier therefor.

9. A sunscreen composition according to claim 8 comprising in the range of from 0.5 to 30% by weight of the compound of formula I.

* * * * *